(12) United States Patent
Heidick

(10) Patent No.: US 6,371,936 B1
(45) Date of Patent: Apr. 16, 2002

(54) CANNULA LOCK WITH PLURAL ACCESS PORTS

(76) Inventor: Mary Annette Heidick, 422 N. 14th St., Fort Dodge, IA (US) 50501

( * ) Notice: Subject to any disclaimer, the term of this patent is extended or adjusted under 35 U.S.C. 154(b) by 0 days.

(21) Appl. No.: 09/338,718

(22) Filed: Jun. 23, 1999

(51) Int. Cl.[7] .................. A61M 37/00; A61M 5/178; A61M 39/02
(52) U.S. Cl. .................. 604/86; 604/539; 604/905; 604/167.02
(58) Field of Search .................. 604/167.01–167.04, 604/201, 256, 284, 523, 533–39, 905, 244, 82–88; 251/149; 138/89, 92

(56) References Cited

U.S. PATENT DOCUMENTS

| | | | | |
|---|---|---|---|---|
| 3,502,097 A | * | 3/1970 | Muller | 137/318 |
| 3,898,988 A | * | 8/1975 | Morgan | 138/103 |
| 4,935,010 A | * | 6/1990 | Cox et al. | |
| 5,163,902 A | * | 11/1992 | Lynn et al. | |
| 5,549,569 A | * | 8/1996 | Lynn et al. | 604/191 |
| 5,788,215 A | * | 8/1998 | Ryan | |
| 6,171,287 B1 | * | 2/2001 | Lynn et al. | |

* cited by examiner

Primary Examiner—Michael J. Hayes
(74) Attorney, Agent, or Firm—McKee, Voorhees & Sease, P.L.C.

(57) ABSTRACT

A cannula lock useful for attachment to a cannula for administration of intravenous fluids to patients. The lock has dual access ports, each closed with a self-healing elastomeric material which can be pierced to introduce fluids into the lock. Having dual openings means one opening can be used for normal saline flushes, and another for injection of medicament fluid. In this way, the lock will last longer and can be more conveniently used at each administration.

3 Claims, 2 Drawing Sheets

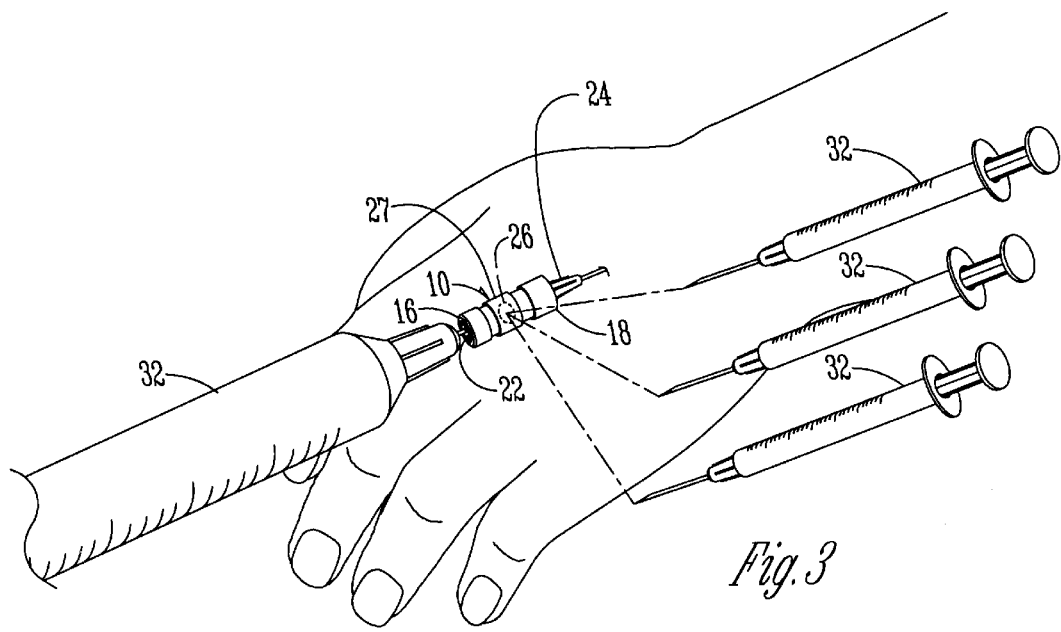
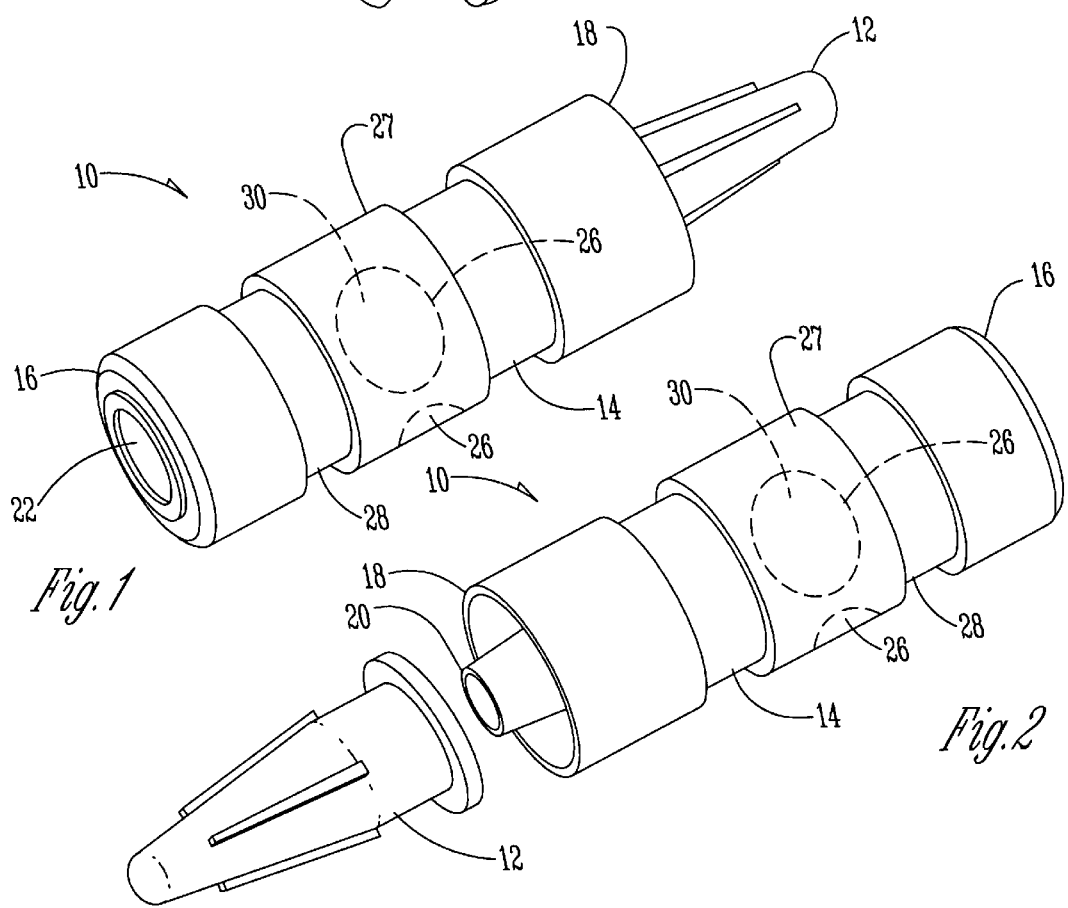

CANNULA LOCK WITH PLURAL ACCESS PORTS

FIELD OF THE INVENTION

The present invention relates to a cannula lock for injection or infusion of medicament flow into a path of parenteral fluid. This allows the same cannula lock to be used simultaneously for flushing with saline solution and introduction of medicaments, each through separate self-healing injection ports in the cannula lock.

BACKGROUND OF THE INVENTION

As is widely known, medicaments are frequently administered as a supplement through the employment of various devices used in conjunction with intravenous administration of fluids to patients. In particular, in order to minimize the amount of bolus injections given a patient, patients are often hooked up with an intravenous cathelon tube (see FIG. 5). In this way, various attachments can be made to the I.V. cathelon for administration of I.V. fluids such as glucose, saline, medicaments of various kinds, etc. Commonly, the devices use a pre-pierced, self-healing male adapter plug with a locking leur, which can be opened, attached to the catheter, and used for continuous I.V. administration (see FIG. 5). When used, such male adapter plugs are used for aseptic introduction of biological fluids in the following manner. The male adapter is opened and connected to the female adapter of the already-inserted cannula (see FIG. 5). It is thereafter tightened, usually by turning clockwise, swabbed with an antiseptic, and thereafter flushed with saline by piercing a resealable membrane with a needle. Thereafter, medication is administered again through the pre-pierced resealable membrane.

As can be seen from the above-described procedure, it involves two piercings of the membrane, one with an original flush of saline solution for cleansing, and a second for injection of medicament fluid into the fluid path or system. In practice, these male adapter plugs are usually changed after about 30 piercings, or three days of use, whichever comes first. In addition, convenience is sacrificed in the present system in that there cannot be co-administration or simultaneous administration of both saline and medicament.

From the above description it can be seen that it would be desirable to provide a piercable, resealable (self-healing) male adapter plug with two or more accessible resealable gates or ports to allow a longer useful life, and to allow co-administration of saline and a medicament. It is a primary objective of the present invention to fulfill this need.

Yet another objective of the present invention is to provide a male adapter plug which can have a useful life at least twice as long as those currently used in hospitals for intravenous administration of parenteral fluids.

The method and means of accomplishing each of the above objectives as well as others will become apparent from the detailed description of the invention which follows hereinafter.

SUMMARY OF THE INVENTION

A cannula lock useful for attachment to a cannula for administration of intravenous fluids to patients. The lock has dual access ports, each closed with a self-healing elastomeric material which can be needle pierced to introduce fluids into the lock. Having dual openings means one opening can be used for normal saline flushes, and another for injection of medicament fluid. In this way, the lock will last longer and can be more conveniently used at each administration.

BRIEF DESCRIPTION OF THE DRAWINGS

FIG. 1 is a perspective view of the pre-pierced, resealable male plug adapter.

FIG. 2 is an exploded view of the pre-pierced male plug adapter with the hood off.

FIG. 3 shows a patient's arm with the inserted cannula having the pierceable, resealable elastomeric, self-healing closure and the pierceable, resealable medicament insert part.

DETAILED DESCRIPTION OF THE INVENTION

Figure 4:
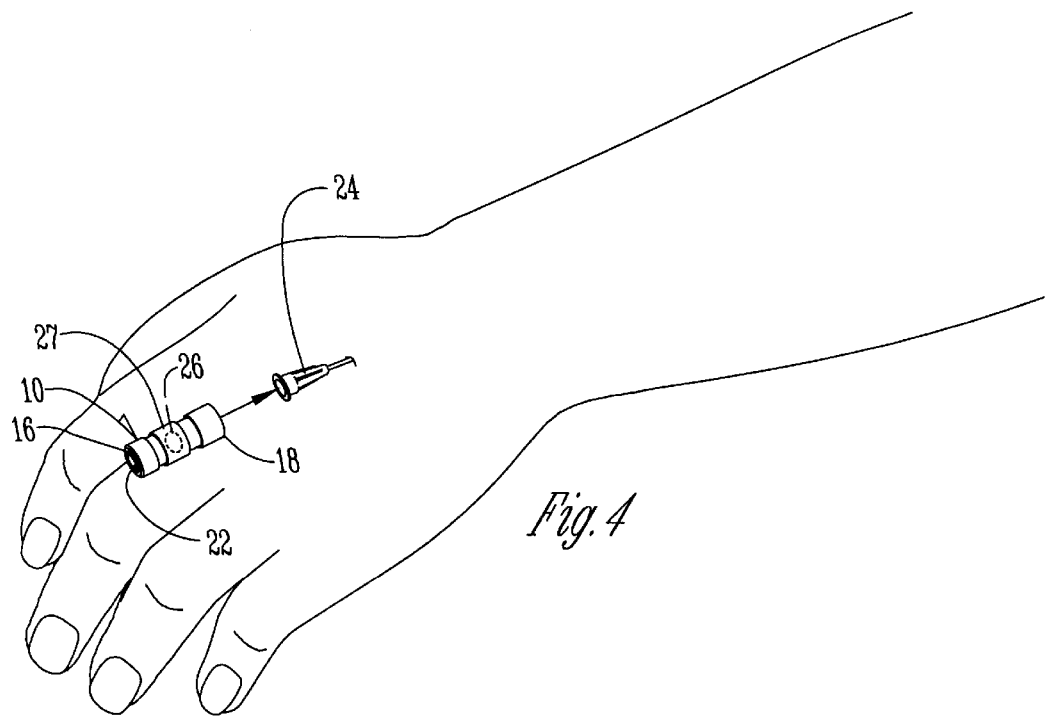
FIG. 4 shows the end opposite the resealable end closure with the cap or hood removed and ready for cannula attachment.

Looking first at FIG. 1, it shows a perspective view of the male adapter plug 10. It may be made of a suitable bio-compatible plastic material such as alpha-olefins like polyethylene and polypropylene, or it can be other suitable bio-compatible plastic materials of known construction such as copolymers of styrene-acrylonitrile or acrylonitrile-butadiene-styrene, etc. Such bio-compatible materials are of known chemical structure, and details of those need not be repeated herein. As can best be seen from the exploded view of FIG. 2, the male plug 10 is comprised of a hood 12, a locking leur 14, with opposing ends 16 and 18. End 18 has a male adapter 20, and end 16 is covered with a self-healing elastomeric rubber material known as the self-healing piercable reseal 22. Piercable resealable material 22 provides a piercable diaphragm of elastomeric material which can be readily pierced by an injection needle for administration of, for example, flushing saline. After the injection or administration the needle is removed, and the diaphragm provides a self-healing closure. Such self-healing buttons of rubber as a closing membrane are known, see for example U.S. Pat. No. 5,033,476, the disclosure of which is incorporated herein by reference, to the extent of its disclosure relating to the self-healing rubber composition.

As explained earlier, in common current use the hood 12 is removed, and the locking leur 14 is attached to the cannula 24 as illustrated in FIG. 3. Typically, flushing occurs with about 1½ cc (cubic centimeters) of saline, and thereafter the same self-healing resealable membrane 22 is used for a second injection with another needle full of medicament, typically at volumes of from 5 cc to 10 cc. This is often followed by yet another saline flush, resulting in three punctures of the membrane for one medicament dose.

The cannula lock or male adapter plug 10 of the present invention has at least one additional access port 26, flush with and built into the sidewall 28 of the chamber 30 of locking plug 10. The second access port 26 is covered with the same self-healing elastomeric material 27 as the self-healing, resealable membrane 22. The elastomeric material has sufficiently thick dimensions to permit resealing after penetration, and yet allow withdrawal of a sharp needle. It also will withstand distortion during sterilization to prevent degradation of the solution during storage and transit.

Figure 5:
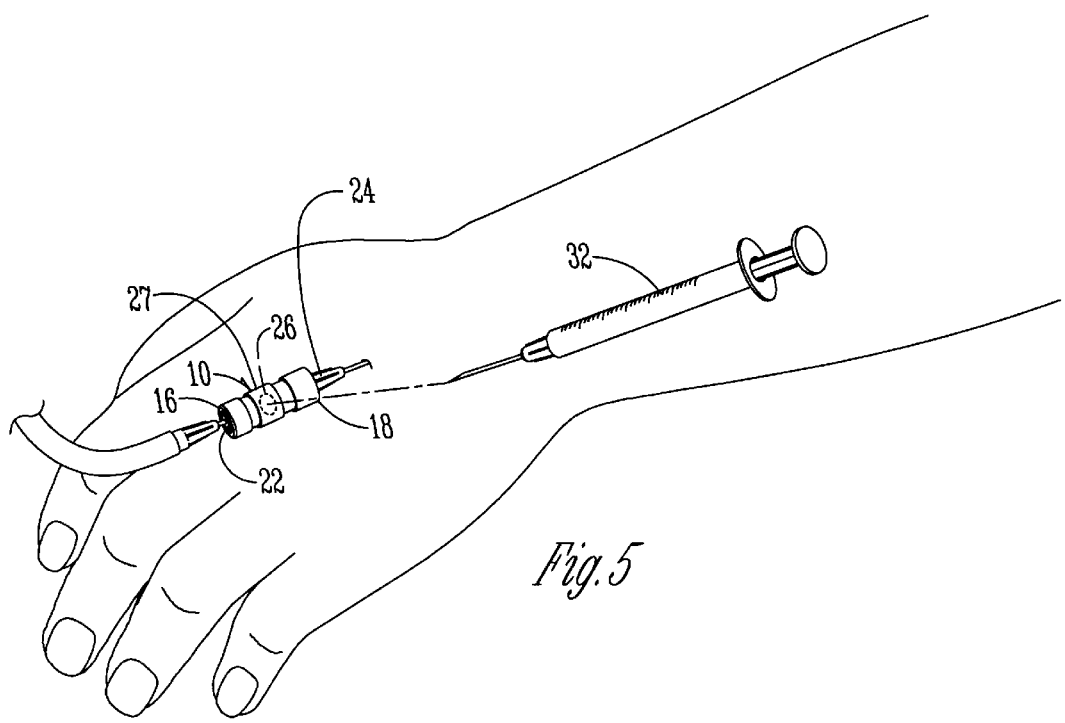
FIG. 5 shows a patient's arm with an inserted cannula and in use with the male adapter plug for co-administration.

Having a second access port 26, preferably in the walled chamber 30 of the male adapter lock 14, allows alteration of the currently-used procedure to a more efficient procedure, for example, illustrated in FIGS. 3 and 5 with use of co-administration syringes 32. In actual operation it is used in the following manner. A sterile package contains the locking leur 10. The package is ripped open with the locking leur 10 removed. The hood 12 is removed by twisting off to reveal the male adapter 20. The male adapter 20 is inserted into the cannula female socket 24 and twisted to attach securely. Saline is flushed through the plug 10 from opposing end 16 resealable membrane 22, typically at a level of 1½ to 2 cc of volume. Either at the same time for co-administration or immediately thereafter, the other access port 26 can be accessed to administer medicaments, typically at a volume of 5 cc to 10 cc. Thereafter, if desired, flushing can occur again through the saline injection insert, and then both needles removed. In this way, medicament and saline can be co-administration and by use of only two membrane piercings (one in each membrane), for the administration. As a result, the male adapter plug can be used with a substantially longer life, and it can be used for co-administration of two biological fluids even at the same time.

If desired, the walled chamber 28 of the cannula lock 10 could also have additional self-healing covered access ports to allow a plurality of administration ports.

What is claimed is:

1. A cannula lock comprising:

a walled chamber wherein the wall is made of biocompatible material having opposing first and second ends;

said first end being sealed with a self-healing elastomeric material which can be pierced to introduce fluid into the lock;

said second end having a male leur adapter and a removable cap associated with the lock which allows said second end to be releasably secured to an intravenous cannula, said lock having at least two access ports formed in the wall of the chamber and flush with an exterior surface of the wall wherein the access ports are sealed with a single exterior self-healing elastomeric membrane to allow for co-administration of one medicament fluid while another fluid is being administered through said first self-healing end.

2. A cannula lock comprising:

a walled chamber wherein the wall is made of biocompatible material having opposing first and second ends;

said first end being sealed with a self-healing elastomeric material which can be pierced to introduce fluid into the lock;

said second end having a male leur adapter and a removable cap associated with the lock which allows said second end to be releasably secured to an intravenous cannula;

said walled chamber having at least two side ports formed in the wall of the chamber and flush with an exterior surface of the wall wherein the side ports are sealed with a single exterior self-healing elastomeric membrane to allow for co-administration of one medicament fluid while another fluid is being administered through said first self-healing end.

3. A method of co-administering parenteral fluids through a cannula comprising:

inserting a cannula having a female end intravenously into a patient's vein; attaching to said female portion of the cannula a cannula lock comprising:

a walled chamber wherein the wall is made of biocompatible material having opposing first and second ends;

said first end being sealed with a self-healing elastomeric material; said second end having a male leur adapter;

said lock having at least two access ports formed in the wall of the chamber and flush with an exterior surface of the wall wherein the access ports are sealed with a single exterior biocompatible, self-healing elastomeric membrane which can be pierced to introduce fluid into the cannula from any port; and piercing the membrane with administration needles to provide co-administration of biologically-active fluids into the cannula; and thereafter withdrawing the administration needles from the pierced, self-healing membrane.

* * * * *